(12) United States Patent
Bormann Chung

(10) Patent No.: US 11,031,099 B2
(45) Date of Patent: Jun. 8, 2021

(54) DETECTION OF SEQUENCE VARIANTS

(71) Applicant: Roche Molecular Systems, Inc., Pleasanton, CA (US)

(72) Inventor: Christina Bormann Chung, San Carlos, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 704 days.

(21) Appl. No.: 15/806,642

(22) Filed: Nov. 8, 2017

(65) Prior Publication Data

US 2018/0129781 A1    May 10, 2018

Related U.S. Application Data

(60) Provisional application No. 62/419,765, filed on Nov. 9, 2016.

(51) Int. Cl.
| | | |
|---|---|---|
| *G16B 30/00* | (2019.01) | |
| *G16B 40/10* | (2019.01) | |
| *C12Q 1/6858* | (2018.01) | |

(52) U.S. Cl.
CPC ........... *G16B 30/00* (2019.02); *C12Q 1/6858* (2013.01); *G16B 40/10* (2019.02)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,851,331 A | 7/1989 | Vary et al. | |
| 4,965,188 A | 10/1990 | Mullis et al. | |
| 5,130,238 A | 7/1992 | Malek et al. | |
| 5,137,806 A | 8/1992 | LeMaistre et al. | |
| 5,210,015 A | 5/1993 | Gelfand et al. | |
| 5,487,972 A | 1/1996 | Gelfand et al. | |
| 5,491,063 A | 2/1996 | Fisher et al. | |
| 5,571,673 A | 11/1996 | Picone | |
| 5,595,890 A | 1/1997 | Newton et al. | |
| 5,639,611 A | 6/1997 | Wallace et al. | |
| 5,804,375 A | 9/1998 | Gelfand et al. | |
| 2005/0130211 A1* | 6/2005 | Shain | C12Q 1/686 435/6.11 |
| 2013/0078626 A1 | 3/2013 | Wasserstrom et al. | |

FOREIGN PATENT DOCUMENTS

| | | |
|---|---|---|
| EP | 0439182 | 7/1991 |
| WO | WO 90/01069 | 2/1990 |
| WO | WO 92/08808 | 5/1992 |
| WO | WO2009086415 | 7/2009 |

OTHER PUBLICATIONS

Zhang et al., PCR microfluidic devices for DNA amplification, 2006, Biotechnology Advances, 24, p. 243-284 (Year: 2006).*
Wolfram, Power Mean, 2020, Wolfram Math World, p. 1-3 (Year: 2020).*
Yu et al., Quantify single nucleotide polymorphism (SNP) ratio in pooled DNA based on normalized fluorescence real-time PCR, 2006, BMC Genomics, 7(143), p. 1-10 (Year: 2006).*
Bio-Rad, iCycler iQ Real-Time PCR Detection System: Instruction Manual, p. 1-39, 2015 (Year: 2015).*
International Search Report PCT/EP2017/078707.
Barany F., Proc. Natl. Acad. Sci. USA 88 (1991)189-193.
Barany F., PCR Methods and Applic. 1 (1991) 5-16.
Kwoh D.Y. et al., Proc. Natl. Acad. Sci. USA 86 (1989) 1173-1177.
Guatelli J.C., et al., Proc. Natl. Acad. Sci. USA 87 (1990) 1874-1878.
Whelen A. C. and Persing D. H., Annu. Rev. Microbiol. 50(1996) 349-373.
Holland et al., 1988, Proc. Natl. Acad. Sci. USA, 88:7276-7280.

* cited by examiner

*Primary Examiner* — Olivia M. Wise
*Assistant Examiner* — Kaitlyn L Minchella
(74) *Attorney, Agent, or Firm* — Pamela C. Ancona

(57) ABSTRACT

Systems, methods, and apparatuses are provided for detecting nucleic acid sequence variants. Other embodiments are directed to systems and computer readable media associated with methods described herein.

10 Claims, 12 Drawing Sheets

$$Log\ DeltaB\ Ratio\ (LDBR) = \log_{10}\left(\frac{DeltaB\ HEX}{DeltaB\ FAM}\right)$$

DETECTION OF SEQUENCE VARIANTS

CROSS-REFERENCE TO RELATED APPLICATION

The present application claims the benefit of priority under 35 U.S.C. § 119 of U.S. Application Ser. No. 62/419,765, filed Nov. 10, 2016, the disclosure of which is incorporated herein by reference in its entirety.

FIELD

The present disclosure relates generally to systems and methods for detecting sequence variants by nucleic acid amplification.

BACKGROUND

The genetic information of all living organisms (e.g., animals, plants and microorganisms) is encoded in deoxyribonucleic acid (DNA). In humans, the complete genome contains of about 100,000 genes located on 24 chromosomes (The Human Genome, T. Strachan, BIOS Scientific Publishers, 1992). Each gene codes for a specific protein, which after its expression via transcription and translation, fulfills a specific biochemical function within a living cell. A change or variation in the genetic code can result in a change in the sequence or level of expression of mRNA and potentially in the protein encoded by the mRNA. These changes, known as polymorphisms or mutations, can have significant adverse effects on the biological activity of the mRNA or protein resulting in disease. Mutations include nucleotide deletions, insertions, substitutions or other alterations (i.e., point mutations).

Many diseases caused by genetic polymorphisms are known and include hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Genetic diseases such as these can result from a single addition, substitution, or deletion of a single nucleotide in the DNA forming the particular gene. In addition to mutated genes, which result in genetic disease, certain birth defects are the result of chromosomal abnormalities such as Trisomy 21 (Down's Syndrome), Trisomy 13 (Patau Syndrome), Trisomy 18 (Edward's Syndrome), Monosomy X (Turner's Syndrome) and other sex chromosome aneuploidies such as Klinefelter's Syndrome (XXY). Further, there is growing evidence that certain DNA sequences can predispose an individual to any of a number of diseases such as diabetes, arteriosclerosis, obesity, various autoimmune diseases and cancer (e.g., colorectal, breast, ovarian, lung).

Certain polymorphisms are thought to predispose some individuals to disease or are related to morbidity levels of certain diseases. Atherosclerosis, obesity, diabetes, autoimmune disorders, and cancer are a few of such diseases thought to have a correlation with polymorphisms. In addition to a correlation with disease, polymorphisms are also thought to play a role in a patient's response to therapeutic agents given to treat disease. For example, polymorphisms are believed to play a role in a patient's ability to respond to drugs, radiation therapy, and other forms of treatment.

Identifying polymorphisms can lead to a better understanding of particular diseases and potentially more effective therapies for such diseases. Indeed, personalized therapy regiments based on a patient's identified polymorphisms can result in life saving medical interventions. Novel drugs or compounds can be discovered that interact with products of specific polymorphisms, once the polymorphism is identified and isolated. The identification of infectious organisms including viruses, bacteria, prions, and fungi, can also be achieved based on polymorphisms, and an appropriate therapeutic response can be administered to an infected host.

Since the sequence of about 16 nucleotides is specific on statistical grounds even for the size of the human genome, relatively short nucleic acid sequences can be used to detect normal and defective genes in higher organisms and to detect infectious microorganisms (e.g., bacteria, fungi, protists and yeast) and viruses. DNA sequences can also serve as a fingerprint for detection of different individuals within the same species (see, Thompson, J. S. and M. W. Thompson, eds., Genetics in Medicine, W.B. Saunders Co., Philadelphia, Pa. (1991)).

Numerous methods have been developed to detect and analyze nucleic acid sequences. For example, nucleic acid sequences can be identified by comparing the mobility of an amplified nucleic acid molecule with a known standard by gel electrophoresis, or by hybridization with a probe which is complementary to the sequence to be identified. An art recognized method of analyzing nucleic acid sequences employs a polymerase chain reaction (PCR), an in vitro method for enzymatically synthesizing or amplifying defined nucleic acid sequences. The reaction typically uses two oligonucleotide primers that hybridize to opposite strands and flank a template or target DNA sequence that is to be amplified. Elongation of the primers is catalyzed by a heat-stable DNA polymerase. A repetitive series of cycles involving template denaturation, primer annealing, and extension of the annealed primers by the polymerase provides an exponential accumulation of a specific DNA fragment. Fluorescent probes or markers are typically used in the process to facilitate detection and quantification of the amplification process In a typical kinetic PCR analysis, fluorescence intensity values are plotted vs. cycle number for a typical PCR process and the formation of PCR products is monitored in each cycle of the PCR process. Amplification is usually measured in thermocyclers which include components and devices for measuring fluorescence signals during the amplification reaction. An example of such a thermocycler is the Roche Diagnostics LightCycler (Cat. No. 20110468). The amplification products are, for example, detected by means of fluorescent-labeled hybridization probes which only emit fluorescence signals when they are bound to the target nucleic acid or, in certain cases, also by means of fluorescent dyes that bind to double-stranded DNA.

However, errors can arise in the data resulting from an amplification reaction, thereby causing errors in the analysis of the data and resulting physical properties (e.g., identification and/or quantification of starting material) obtained from the analysis. Moreover, when analyzing relatively small sequence variations in a large population of nucleic acids, these errors can be compounded. Therefore, it would be beneficial to identify an improved process for analyzing sequence variant information using the output of nucleic acid amplification methods.

BRIEF SUMMARY

The disclosure provides a system for detecting two or more nucleic acid sequence variants in a sample, the system including a nucleic acid amplification module operably connected to a memory, a processor, and a display. The system is configured to perform a method of detecting the two or more sequence variants by amplifying, using the nucleic acid amplification module, the at least two sequence variants to produce at least two amplification products including a first variant amplicon and a second variant amplicon and generating, using the processor, a first and second growth curve, respectively, for the first and second amplicons. The growth curves are analyzed, using the processor, to determine the relative deviation from linearity of the first and second growth curves by generating a first deviation from linearity of the first growth curve and a second deviation from linearity of the second growth curve and comparing the first and second deviations to generate a deviation from linearity ratio. Using the processor, the system then compares the relative deviation from linearity to a threshold matrix and thereby identifies the two or more sequence variants.

Also provided is a system for detecting two or more nucleic acid sequence variants in a sample, wherein the system comprises a nucleic acid amplification module operably connected to a memory, a processor, and a display. The nucleic acid amplification module amplifies the at least two sequence variants to produce at least two amplification products including a first variant amplicon and a second variant amplicon and generating, using the processor, a first and second growth curve, respectively, for the first and second amplicons. Thereafter, the processor is configured to receive a first dataset representing a growth curve for amplification of a first nucleic acid variant; receive a second dataset representing a growth curve for amplification of an additional nucleic acid variant, wherein said additional nucleic acid variant comprises said at least one sequence modification at a polymorphic site relative to the first nucleic acid variant; generate a first curve that fits said first dataset and a second curve that fits said second dataset; generate a first deviation from linearity of the first curve and a second deviation from linearity of the second curve; compare the first deviation from linearity to the second deviation from linearity to identify a deviation from linearity ratio; compare the deviation from linearity ratio to a threshold matrix; and identify the two or more sequence variant based on the comparison to the threshold matrix.

A further embodiment is a method of detecting at least two nucleic acid sequence variants in a sample, the method comprising the steps: amplifying the at least two sequence variants to produce at least two amplification products including a first variant amplicon and a second variant amplicon, wherein the amplifying step yields a first and second growth curve, respectively, for the first and second amplicons; analyzing, using a processor, the relative deviation from linearity of the first and second growth curves by generating a first deviation from linearity of the first growth curve and a second deviation from linearity of the second growth curve and comparing the first and second deviations from linearity to generate a deviation from linearity ratio; comparing, using the processor, the relative deviation from linearity to a threshold matrix; and identifying, using the processor based on the results of comparing step, the two or more sequence variants.

Yet another embodiment is a computer-implemented method of detecting two or more sequence variants, the method comprising, at a computer system: receiving a first dataset representing a growth curve for amplification of a first nucleic acid variant; receiving a second dataset representing a growth curve for amplification of an additional nucleic acid variant, wherein said additional nucleic acid variant comprises said at least one sequence modification at a polymorphic site relative to the first nucleic acid variant; generating a first curve that fits said first dataset and a second curve that fits said second dataset; generating a first deviation from linearity of the first curve and a second deviation from linearity of the second curve; comparing the first deviation from linearity to the second deviation from linearity to identify a deviation from linearity ratio; comparing the deviation from linearity ratio to a threshold matrix; and identifying the two or more sequence variants based on said comparing step.

A better understanding of the nature and advantages of the present disclosure may be gained with reference to the following detailed description and the accompanying drawings.

DETAILED DESCRIPTION

Figure 1:
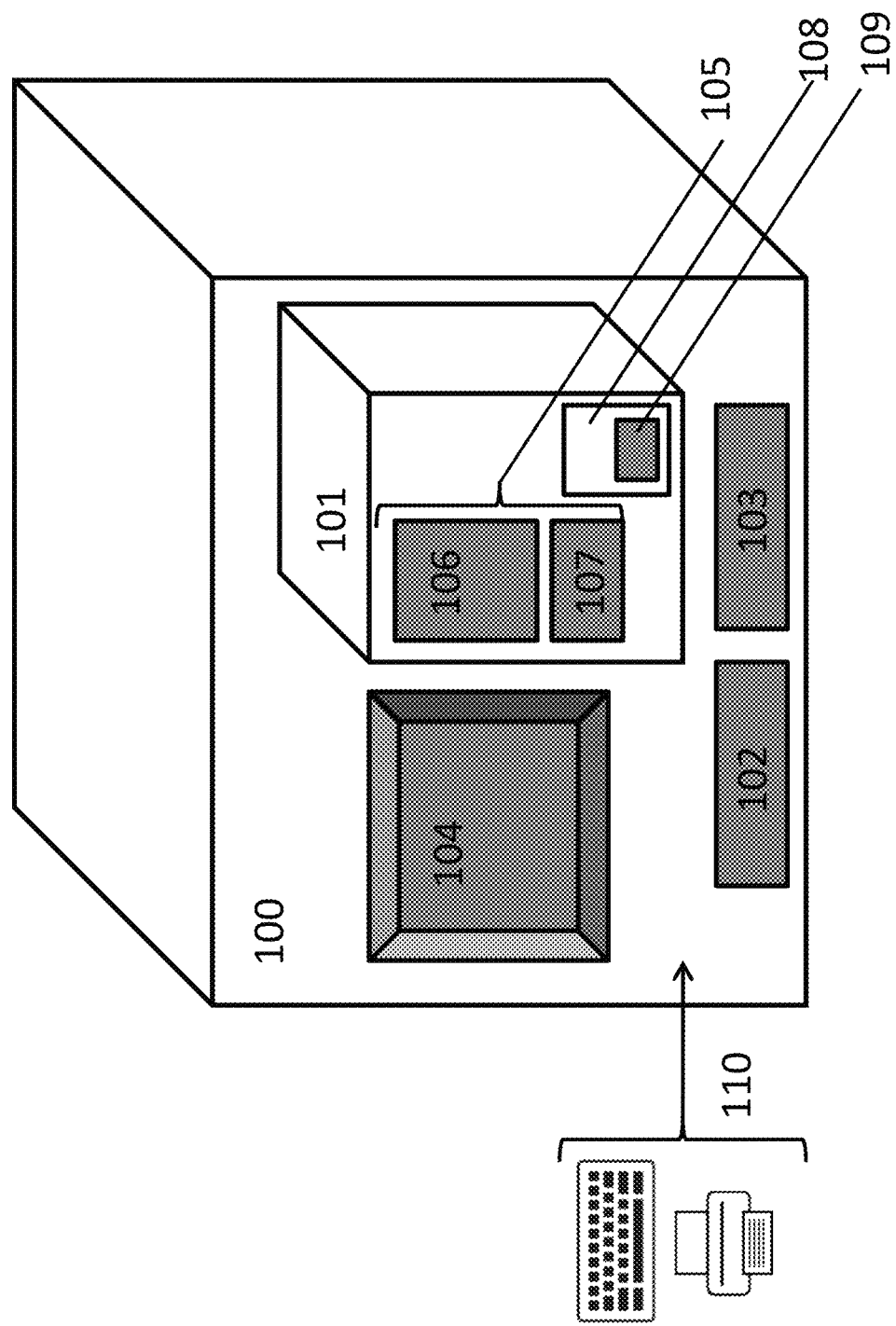
FIG. 1 is a block diagram of a system as described herein.

Embodiments can detect sequence variants based on a nucleic acid amplification reaction. Conventional methods inaccurately identify sequence variants, whereas the improved methods described herein provide a mechanism to consistently and accurately identify variants that were not correctly detected using conventional methods. Moreover, the improved methods have been found to be more robust when challenging samples are evaluated, e.g., in the presence of potentially inhibiting components.

Unless otherwise defined herein, scientific and technical terms used herein have the meanings that are commonly understood by those of ordinary skill in the art. Further, unless otherwise required by context, singular terms include pluralities and plural terms include the singular. The articles "a" and "an" are used herein to refer to one or to more than one (i.e., to at least one) of the grammatical object of the article. By way of example, "an element" means one element or more than one element.

The terms "detect," "detecting," "detection," and similar terms are used in this application to broadly refer to a process or discovering or determining the presence or an absence, as well as a degree, quantity, or level, or probability of occurrence of something. For example, the term "detecting" when used in reference to a target nucleic acid sequence, can denote discovery or determination of the presence, absence, level or quantity, as well as a probability or likelihood of the presence or absence of the sequence. It is to be understood that the expressions "detecting presence or absence," "detection of presence or absence" and related expressions include qualitative and quantitative detection.

The terms "nucleic acid," "polynucleotide," and "oligonucleotide" refer to polymers of nucleotides (e.g., ribonucleotides or deoxyribo-nucleotides) and includes naturally-occurring (adenosine, guanidine, cytosine, uracil and thymidine), non-naturally occurring, and modified nucleic acids. The term is not limited by length (e.g., number of monomers) of the polymer. A nucleic acid may be single-stranded or double-stranded and will generally contain 5'-3' phosphodiester bonds, although in some cases, nucleotide analogs may have other linkages. Monomers are typically referred to as nucleotides. The term "non-natural nucleotide" or "modified nucleotide" refers to a nucleotide that contains a modified nitrogenous base, sugar or phosphate group, or that incorporates a non-natural moiety in its structure. Examples of non-natural nucleotides include dideoxynucleotides, biotinylated, aminated, deaminated, alkylated, benzylated and fluorophor-labeled nucleotides.

Suitable nucleic acid amplification methods that may include the use of the standards described herein include, but are not limited to, the Ligase Chain Reaction (LCR; Wu D. Y. and Wallace R. B., Genomics 4 (1989) 560-69; and Barany F., Proc. Natl. Acad. Sci. USA 88 (1991)189-193); Polymerase Ligase Chain Reaction (Barany F., PCR Methods and Applic. 1 (1991) 5-16); Gap-LCR (WO 90/01069); Repair Chain Reaction (EP 0439182 A2), 3SR (Kwoh D. Y. et al., Proc. Natl. Acad. Sci. USA 86 (1989) 1173-1177; Guatelli J. C., et al., Proc. Natl. Acad. Sci. USA 87 (1990) 1874-1878; WO 92/08808), and NASBA (U.S. Pat. No. 5,130,238). Further, one or more of the following methods can also be used: strand displacement amplification (SDA), transcription mediated amplification (TMA), and Qb-amplification (for a review see e.g. Whelen A. C. and Persing D. H., Annu. Rev. Microbiol. 50(1996) 349-373; Abramson R. D. and Myers T. W., Curr Opin Biotechnol 4 (1993) 41-47).

As described above, in a specific embodiment, nucleic acid sequences are analyzed by PCR, disclosed, e.g., in U.S. Pat. Nos. 4,683,202, 4,683,195, 4,800,159, and 4,965,188, among other references. The disclosures of these references are incorporated herein by reference in their entirety. PCR typically employs two or more oligonucleotide primers that bind to a selected nucleic acid template (e.g. DNA or RNA). Primers useful for nucleic acid analysis include oligonucleotides capable of acting as a point of initiation of nucleic acid synthesis within the nucleic acid sequences of the target nucleic acids. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating. A "thermostable polymerase" is a polymerase enzyme that is heat stable, i.e., it is an enzyme that catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have, for example, been isolated from *Thermus flavus, T. ruber, T. thermophilus, T. aquaticus, T. lacteus, T. rubens, Bacillus stearothermophilus,* and *Methanothermus fervidus*. Nonetheless, polymerases that are not thermostable also can be employed in PCR assays provided the enzyme is replenished.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured. The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 5 sec to 9 min.

If the double-stranded template nucleic acid is denatured by heat, the reaction mixture is allowed to cool to a temperature that promotes annealing of each primer to its target sequence on the target nucleic acids. The temperature for annealing is preferably from about 35° C. to about 70° C., further preferably about 45° C. to about 65° C.; further preferably about 50° C. to about 60° C., further preferably about 55° C. to about 58° C. Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the nucleic acid to be analyzed. The temperature should be sufficient to synthesize an extension product from each primer that is annealed to a nucleic acid template, but should not be so high as to denature an extension product from its complementary template (e.g., the temperature for extension generally ranges from about 40° to 80° C. (e.g., about 50° C. to about 70° C.; about 60° C.). Extension times can be from about 10 sec to about 5 min, preferably about 15 sec to 2 min, further preferably about 20 sec to about 1 min, further preferably about 25 sec to about 35 sec.

The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acids. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated about 20 times, but may be repeated fewer than 20 times or as many as 40, 60, or even 100 times. Moreover, a PCR assay can be carried out in which the steps of annealing and extension are performed in the same step (one-step PCR) or, in separate steps (two-step PCR).

The term "sample" refers to any composition containing or presumed to contain nucleic acid from an individual. The term includes purified or separated components of cells, tissues, or blood and blood components, e.g., DNA, RNA, proteins, cell-free portions, cell lysates, plasma, platelets, serum, buffy coat, and dried blood spots. Samples also may include constituents and components of in vitro cultures of cells obtained from an individual, including cell lines. Specific additional examples of samples include feces, mucosal swabs, tissue aspirates, tissue homogenates, cell cultures and cell culture supernatants (including cultures of eukaryotic and prokaryotic cells), urine, saliva, sputum, and cerebrospinal sample.

The methods described herein can be used to identify nucleic acid sequence variants. Various types of sequence variants can be identified, including but not limited to, alleles, polymorphisms, haplotypes, and/or genotypes. The term "allele" refers to a sequence variant of a gene. One or more genetic differences can constitute an allele. The term "polymorphism" refers to the condition in which two or more variants of a specific nucleotide sequence can be found in a population. A polymorphic position refers to a site in the nucleic acid sequence where the polymorphic nucleotide that distinguishes the variants occurs. A "single nucleotide polymorphism" or SNP, refers to a polymorphic site consisting of a single nucleotide. The term "haplotype" refers to a combination of alleles at different places (loci or genes) on the same chromosome in an individual, whereas the term "genotype" refers to the sum of the alleles of the gene contained in an individual or a sample.

In the methods described herein, sequence variants can be identified by detecting the nucleotide present at one or more of polymorphic sites. Any type of tissue containing the nucleic acid(s) of interest may be used. A number of methods are known in the art for identifying sequence anomalies and the particular method used is not a critical aspect of the disclosure. Exemplary methods involve allele-specific amplification or probe-based detection of amplified nucleic acid.

In one embodiment, alleles can be identified using allele-specific amplification or primer extension methods, which are based on the inhibitory effect of a terminal primer mismatch on the ability of a DNA polymerase to extend the primer. To detect an allele sequence using an allele-specific amplification or extension-based method, a primer complementary to each of the allelic genes is chosen such that the 3' terminal nucleotide hybridizes at the polymorphic position. In the presence of the target allele, the primer matches the target sequence at the 3' terminus and primer is extended. In the presence of another allele, the primer has a 3' mismatch relative to the target sequence and primer extension is either eliminated or significantly reduced. Allele-specific amplification- or extension-based methods are described in, for example, U.S. Pat. Nos. 5,137,806; 5,595,890; 5,639,611; and 4,851,331, each incorporated herein by reference. Allele-specific amplification-based methods of genotyping can facilitate the identification of haplotypes. Essentially, allele-specific amplification is used to amplify a region encompassing multiple polymorphic sites from one of the two alleles in a heterozygous sample. The SNP variants present within the amplified sequence are then identified, such as by probe hybridization or sequencing.

In another embodiment, probe-based methods are used, which rely on the difference in stability of hybridization duplexes formed between a probe and its corresponding target sequence comprising multiple target alleles. Under sufficiently stringent hybridization conditions, stable duplexes are formed only between a probe and its target allele sequence and not with other allele sequences. The presence of stable hybridization duplexes can be detected by any of a number of well-known methods. In a specific embodiment, multiple nucleic acid sequences from the target allelic genes which encompass the polymorphic sites are amplified and hybridized to a set of probes under sufficiently stringent hybridization conditions. The alleles present are inferred from the pattern of binding of the probes to the amplified target sequences. In this embodiment, amplification is carried out in order to provide sufficient nucleic acid for analysis by probe hybridization. Thus, primers are designed such that regions of the various allelic genes encompassing the polymorphic sites are amplified regardless of the allele present in the sample. Allele-independent amplification is achieved using primers which hybridize to conserved regions of the allelic genes. One of skill will recognize that, typically, experimental optimization of an amplification system is helpful.

Probe-based genotyping can be carried out using a "TaqMan" or "5'-nuclease assay," as described in U.S. Pat. Nos. 5,210,015; 5,487,972; and 5,804,375; and Holland et al., 1988, Proc. Natl. Acad. Sci. USA, 88:7276 7280, each incorporated herein by reference. In the TaqMan assay, labeled detection probes that hybridize within the amplified region are added during the amplification reaction mixture. The probes are modified so as to prevent the probes from acting as primers for DNA synthesis. The amplification is carried out using a DNA polymerase that possesses 5' to 3' exonuclease activity, e.g., Tth DNA polymerase. During each synthesis step of the amplification, any probe which hybridizes to the target nucleic acid downstream from the primer being extended is degraded by the 5' to 3' exonuclease activity of the DNA polymerase. Thus, the synthesis of a new target strand also results in the degradation of a probe, and the accumulation of degradation product provides a measure of the synthesis of target sequences.

In a specific embodiment, the detection probes are labeled with two fluorescent dyes, one of which is capable of quenching the fluorescence of the other dye. The dyes are attached to the probe, preferably one attached to the 5' terminus and the other is attached to an internal site, such that quenching occurs when the probe is in an unhybridized state and such that cleavage of the probe by the 5' to 3' exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated herein by reference, describe alternative methods for detecting the degradation of probe which occurs concomitant with amplification.

The TaqMan assay can be used with allele-specific amplification primers such that the probe is used only to detect the presence of amplified product. Such an assay is carried out as described for the kinetic-PCR-based methods described above. Alternatively, the TaqMan assay can be used with a target-specific probe.

Regardless of the underlying assay method, the systems and methods described herein identify specific sequence variants present in a sample by comparing the relative deviation from linearity of the PCR growth curves for each sequence analyzed and comparing that value to a defined threshold matrix for the sequence variants that may be present in the sample.

FIG. 1 shows a block diagram of a system 100 for detecting at least one sequence variant in a target nucleic acid sequence including a nucleic acid amplification module 101, memory 102, a processor 103, and a display 104. The nucleic acid amplification module 101 includes one or more sample processing modules 105. Each sample processing module 105 comprises one or more units or stations for carrying out the various steps required to process a sample including one or more nucleic acid sequences for analysis. The sample processing module 105 includes a reaction chamber 106 and a thermoelectric cooling device 107, e.g., a thermal cycler, and optionally one or more of the following (not shown): a sample dispensing station, a separation station, and one or more consumable and/or reagent storage stations. The reaction chamber is configured to house a sample during one or more nucleic acid amplification reaction steps. In addition, the nucleic acid amplification module 101 also includes at least one control unit 108 electrically connected to one or more of the sample processing modules. The control unit 108 also includes an analysis module 109 configured to analyze a nucleic acid to obtain a detectable signal.

Memory 102 can include any combination of any type of volatile or non-volatile memory, such as random-access memories (RAMs), read-only memories such as an Electrically-Erasable Programmable Read-Only Memory (EEPROM), flash memories, hard drives, solid state drives, optical discs, and the like. For brevity, memory 102 is depicted in FIG. 1 as a single device, but it is appreciated that memory 102 can also be distributed across two or more devices. Processor 103 can include one or more processors of any type, such as central processing units (CPUs), graphics processing units (GPUs), special-purpose signal or image processors, field-programmable gate arrays (FPGAs), tensor processing units (TPUs), and so forth. While processor 103 is depicted in FIG. 1 as a single device, processor 103 can also be distributed across any number of devices. Display 104 can be implemented using any suitable technology, such as LCD, LED, OLED, TFT, Plasma, etc. In some implementations, display 104 may be a touch-sensitive display (a touchscreen).

The system 100 can also be operably connected to one or more computing devices (not shown) such as desktop computers, laptop computers, tablets, smartphones, servers, application-specific computing devices, or any other type(s) of electronic device(s) capable of performing the techniques and operations described herein. In some embodiments, the elements of the system and the subcomponents of each element can be provided in a single device or as a combination of two or more devices together achieving the various functionalities discussed herein. For example, nucleic acid amplification module 101 may include one or more server computers and a one or more client computers communicatively coupled to each other via one or more local-area networks and/or wide-area networks. Finally, the system 100 can also include one or more peripheral devices 110 (e.g., a printer 111 and keyboard 112, as shown in FIG. 1), and the computer subsystems can be interconnected via a system bus. Peripherals and input/output (I/O) devices, which couple to an I/O controller, can be connected to the system 100 by any means known in the art, such as a serial port. For example, a serial port or external interface (e.g. Ethernet, Wi-Fi, etc.) can be used to connect the system 100 to a wide area network such as the Internet, a mouse input device, or a scanner. The interconnection via system bus allows the central processor 103 to communicate with each subsystem and to control the execution of instructions from system memory 102 or the storage device(s) (not shown), as well as the exchange of information between subsystems. The system memory and/or the storage device(s) may embody a computer readable medium. Any of the values mentioned herein can be output from one component to another component and can be output to the user.

A computer system can include a plurality of the same components or subsystems, e.g., connected together by external interface or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present disclosure can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present disclosure may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

Figure 2A:
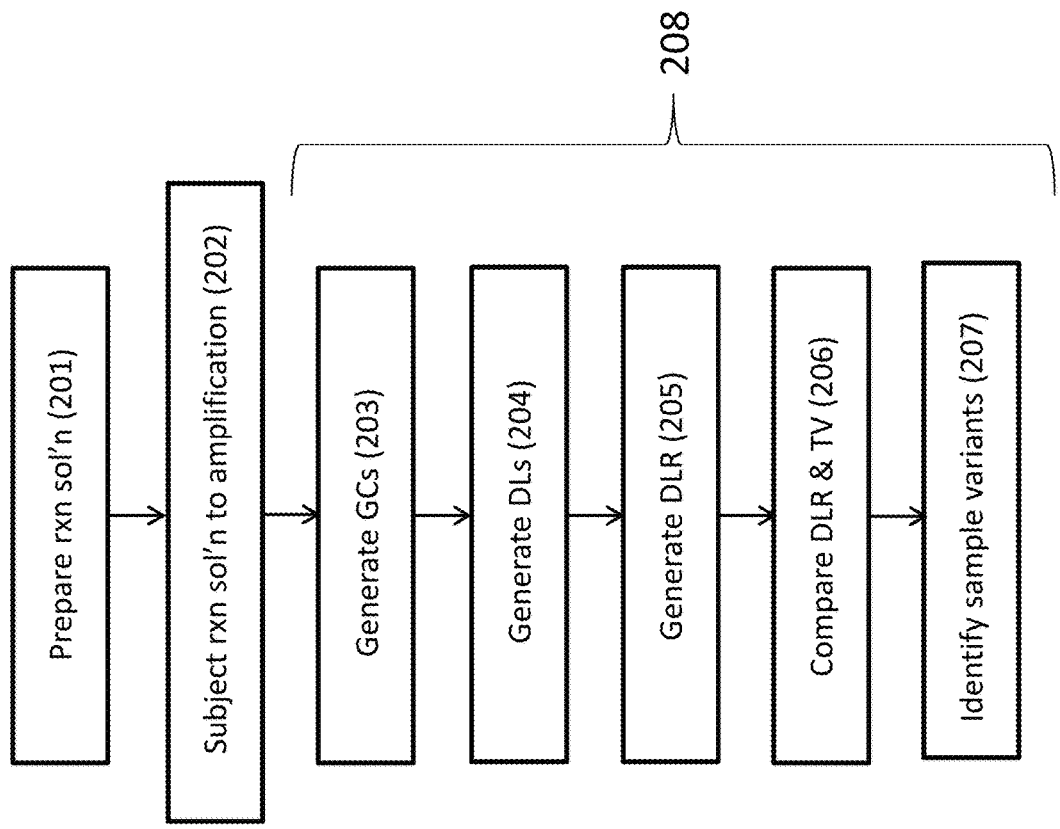
FIG. 2(a) is a schematic illustration of the method employed by the system.

FIG. 2(a) illustrates a method used by the system of FIG. 1 to detect sequence variants of a target nucleic acid sequence. Once a sample is received and appropriately processed, e.g., combining the various nucleic acids present in the sample with one or more primers and probes and additional reaction components required to conduct a nucleic acid amplification reaction (201), the nucleic acids in the sample are subjected to an amplification reaction and each nucleic acid is identified using a detectable moiety, e.g., a distinct fluorescent dye (202). In a specific embodiment, at least two nucleic acids are present in the sample, e.g., a first variant and a second variant, and each is uniquely identifiable in the amplification reaction using a different detectable moiety. Optionally, the method also includes a control substance, e.g., a housekeeping gene, which is also uniquely labeled so that it can be differentially detected in the amplification reaction. The system generates growth curves (GCs; 203) for each amplification reaction and then the processor determines a deviation from linearity (DL; 204) of each growth curve. The deviations from linearity are compared to one another to identify a deviation from linearity ratio (DLR; 205), i.e., a comparison of the relative deviation from linearity of each dataset, and the deviation from linearity ratio is then compared to a pre-defined threshold matrix specific for the target nucleic acid sequence (206) to identify the specific sequence variants present in the sample (207).

Figure 2B:
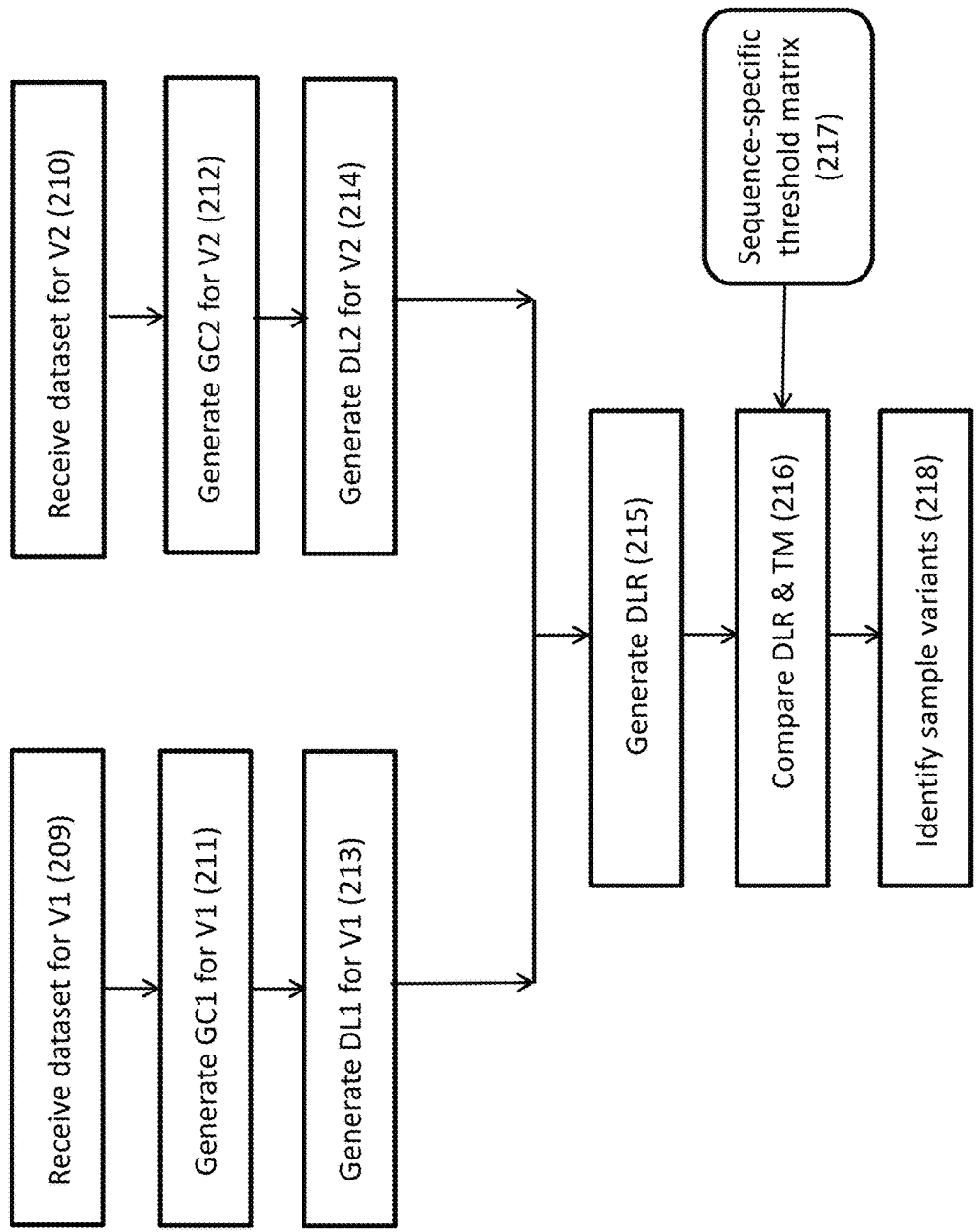
FIG. 2(b) is a schematic illustration of the data processing portion of the method.

Steps 203-207 comprise the data analysis components of the method (208) and these steps are illustrated in more detail in FIG. 2(b). The processor receives a first dataset for a first nucleic acid amplification reaction of a first variant (V1) (209) as well as a second dataset for a second nucleic acid amplification reaction of a second variant (V2) (210). Each of the datasets are used by the processor to generate a growth curve for each amplification reaction (211 and 212), and a deviation from linearity for each growth curve is subsequently generated by the processor (213 and 214). By comparing the deviations from linearity of the growth curves, the processor generates a deviation from linearity ratio (215), which is then compared (216) to a sequence-specific threshold matrix (TM) (217) to identify the sequence variants present in the sample (218).

The sequence-specific threshold matrix (217) is determined by analyzing the individual growth curves of a plurality of known specific nucleic acid sequences. For example, if two variants will be evaluated, a pool of samples of each variant are analyzed to identify the expected growth curves for those sequences. Then the deviation from linearity ratio for each possible variant of interest relative to the other(s) is determined and this data is used to generate a sequence-specific threshold matrix. Additionally, the threshold matrix can also include an evaluation of other characteristics of a growth curve, such as, but not limited to, deltaCTR or delta CT. The cycle threshold value (CT) is the number of cycles required for the detectable signal to cross the threshold, exceeding the background level, indicating that amplification has commenced. The CT is specific for the amount of nucleic acid present in the reaction. The delta CT corresponds to the difference between CT of a nucleic acid being evaluated versus that of a reference sequence. The growth curve shape can be specific for a specific sequence of interest, primers, probe, and thermocycling conditions. The threshold matrix includes a set of acceptable deviation from linearity ratio ranges for each variant under evaluation.

Figure 3:
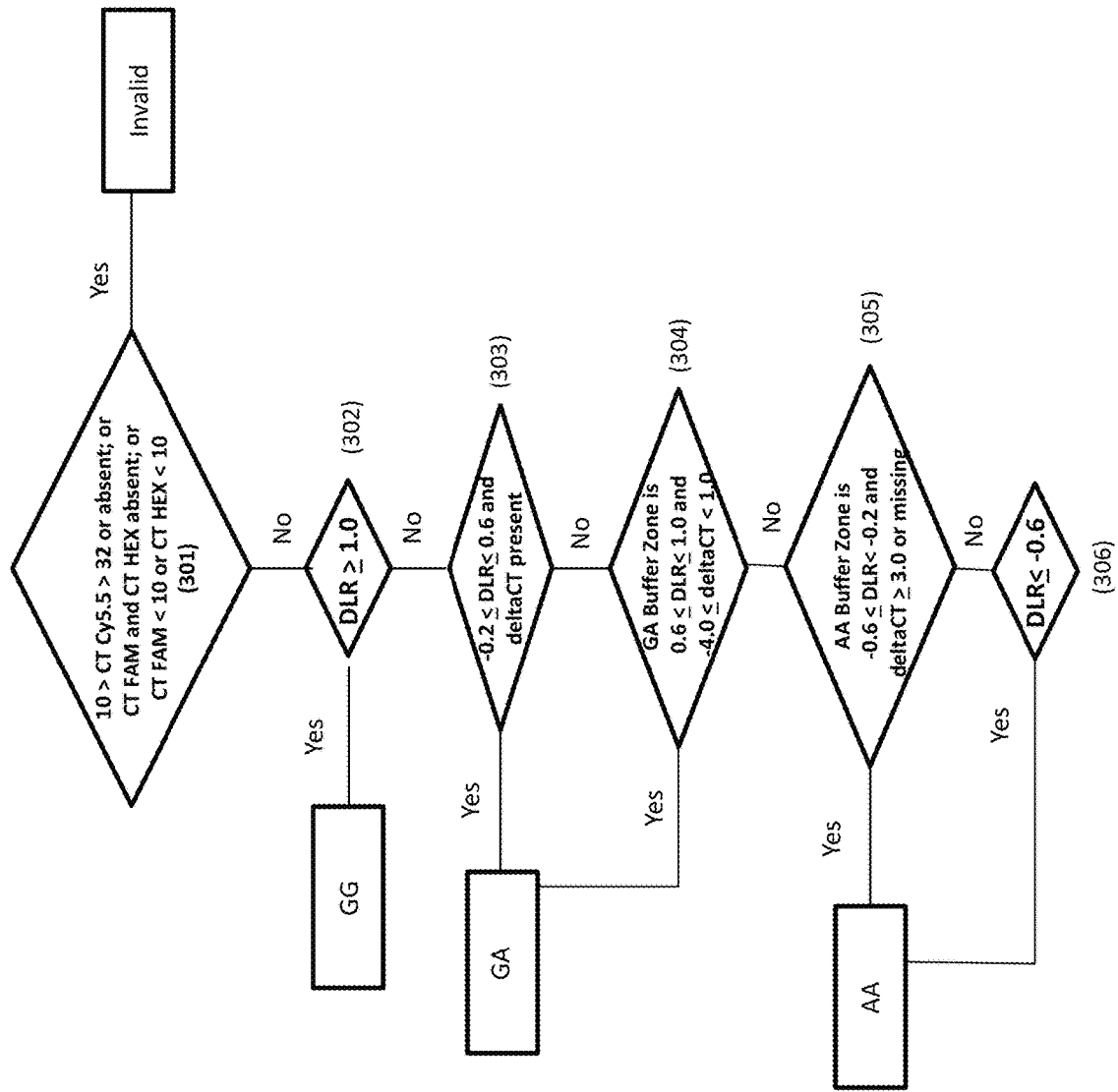
FIG. 3 is an illustration of a specific example of the use of the sequence specific threshold matrix.

For example, as described in more detail in the Example below, a threshold matrix can be used to distinguish among different alleles in a sequence, e.g., GG, GA, and AA, as shown in FIG. 3. The nucleic acid amplification is conducted in three channels in the nucleic acid amplification module, each channel configured to detect a different allele using a distinct detectable label. For example, the first channel can include a control identified using, e.g., Cy5.5, the second channel is used to evaluate the presence of G, detectably labeled with HEX, and the third channel is used to evaluate the presence of A, detectably labeled with FAM. (The specific alleles and choice of detectable labels are non-limiting and provided herein for illustrative purposes only.) The threshold matrix includes a set of acceptable ranges for the deviation from linearity ratios of each allele, therefore, for the three alleles being evaluated in this example, the matrix will include a GG range, a GA range, and an AA range. At the juncture between two ranges there can be a range referred to as the buffer zone which is a region of the matrix where if a deviation from linearity ratio falls within that zone, one or more additional calculations can be employed to further confirm the identity of the allele.

If empirically valid results are obtained following amplification in each channel (301), e.g., the growth curve CT for the control channel is not outside of a specified range or absent, CT for FAM and HEX are not both absent, and individual CTs for FAM and HEX are not outside of a specified range, then the linearity ratio is evaluated as follows:

If the linearity ratio is greater than or equal to 1.0 (302), then the allele is GG;
If the linearity ratio is between −0.2 and 0.6 and a deltaCT is present (303), then the allele is GA;
If the linearity ratio in the GA buffer zone is between 0.6 and 1.0 and the deltaCT is between −4.0 and 1.0 (304), then the allele is GA;
If the linearity ratio in the AA buffer zone is between −0.6 and −0.2 and the deltaCT is greater than or equal to 3.0 or missing (305), then the allele is AA; or
If the linearity ratio is less than or equal to −0.6 (306), then the allele is AA.

In a specific embodiment, the method includes a calculation of deltaB, which is defined as the relative maximum deviation from linearity of a straight line, $\hat{y}=a+bx$, from the nucleic acid amplification data over a range of cycle numbers. Accordingly, deltaB can be used to calculate the deviation from linearity of a growth curve for nucleic acid n, e.g., $$\text{deltaB}n = (\text{maximum}|\hat{y}i - yi|/\text{generalized mean of baseline})$$

where n corresponds to the nucleic acid being analyzed and the generalized mean of the baseline comprises yMedian, geometric mean, harmonic mean, or generalized mean, and in a specific embodiment, the generalized mean of the baseline is yMedian. Hence, deltaB can be represented as follows:

$$\text{deltaB}n = (\text{maximum}|\hat{y}i - yi|/y\text{Median}).$$

The deviation from linearity is preferably evaluated over a range of cycle numbers, e.g., from cycles m to p wherein $0 < m < p$. In one embodiment, $m \geq 2$, particularly, $3 \leq m \leq 7$, and preferably $m = 6$.

Therefore, in this embodiment, the deviation from linearity ratio, which reflects the relative approximate deviation from linearity of two growth curves representing amplification of a first and second nucleic acid, can be calculated as:

Deviation from linearity ratio=deltaB$_1$/deltaB$_2$.

In a particular embodiment, the deviation from linearity ratio comprises:

log 10(deltaB1/deltaB2).

Thus, one example of the deviation from linearity ratio is a Log DeltaB Ratio (LDBR). It has been surprisingly found that the use of a deviation from linearity ratio such as LDBR enables the RFI (relative fluorescence intensity) to be lowered relative to a conventional algorithm and it identifies sequence variants with a higher degree of sensitivity than conventional methods based on a comparison to Sanger sequencing. LDBR was found to be more robust in identifying correct genotypes instead of invalid or incorrect results, when challenging samples with one or more materials or conditions that have been found to introduce genotyping errors using conventional logic.

Accordingly, in the systems and methods described herein, a method is performed by a processor comprising (a) Receiving a first dataset representing a growth curve for amplification of a first nucleic acid variant; (b) Receiving a second dataset representing a growth curve for amplification of an additional nucleic acid variant, wherein said additional nucleic acid variant comprises said at least one sequence modification at a polymorphic site relative to the first nucleic acid variant; (c) Generating a first curve that fits said first dataset and a second curve that fits said second dataset; (d) Generating a deltaB of the first curve and a deltaB of the second curve; (e) Comparing the deltaB for the first and second curves by taking the log$_{10}$ of the ratio of deltaB for the first and second curves to derive the LDBR; (f) Comparing the LDBR to a threshold matrix; and (g) Identifying the two or more sequence variants based on said comparing step (f).

The specific details of particular embodiments may be combined in any suitable manner without departing from the spirit and scope of embodiments of the disclosure. However, other embodiments of the disclosure may be directed to specific embodiments relating to each individual aspect, or specific combinations of these individual aspects.

The above description of exemplary embodiments of the disclosure has been presented for the purposes of illustration and description. It is not intended to be exhaustive or to limit the disclosure to the precise form described, and many modifications and variations are possible in light of the teaching above. The embodiments were chosen and described in order to best explain the principles of the disclosure and its practical applications to thereby enable others skilled in the art to best utilize the disclosure in various embodiments and with various modifications as are suited to the particular use contemplated.

All patents, patent applications, publications, and descriptions mentioned here are incorporated by reference in their entirety for all purposes. None is admitted to be prior art.

EXAMPLE

Algorithm Selection and Cut-Off Determination for Genotyping Assay

Figure 4:
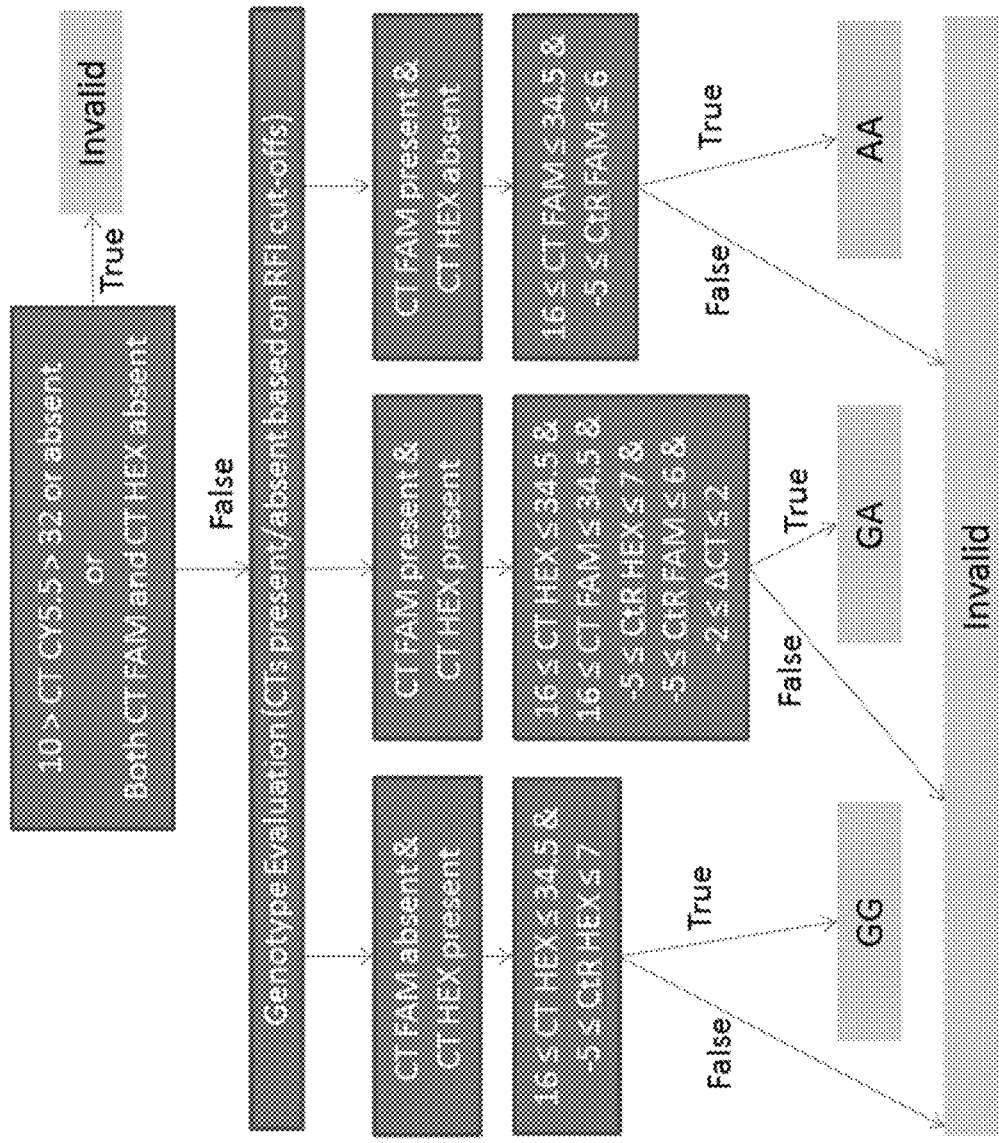
FIG. 4 illustrates a specific example of conventional sequence variant logic.

It was found that conventional genotype logic identified incorrect genotypes under stress conditions (e.g., when PCR inhibitors were spiked into the sample). These incorrect results were due to variation in RFI (Relative Fluorescence Intensity) values in either FAM (6-carboxyfluorescein with a threonine linker) or HEX (Hexachloro-fluorescein with a threonine linker) channels in a Cobas® 4800 System, resulting in crossing the RFI cut-offs. Using conventional methods, if an RFI value was below the cut-off, CT values were removed for this channel. Subsequently, genotypes were determined on CT values present in only a subset of the channels (see, e.g., FIG. 4). For example, if the FAM RFI value dropped below the cut-off in a heterozygous specimen GA, only HEX and CY5.5 CTs would be present, resulting in an incorrect identification of the GG genotype, if all other values were within specifications.

Figure 5:
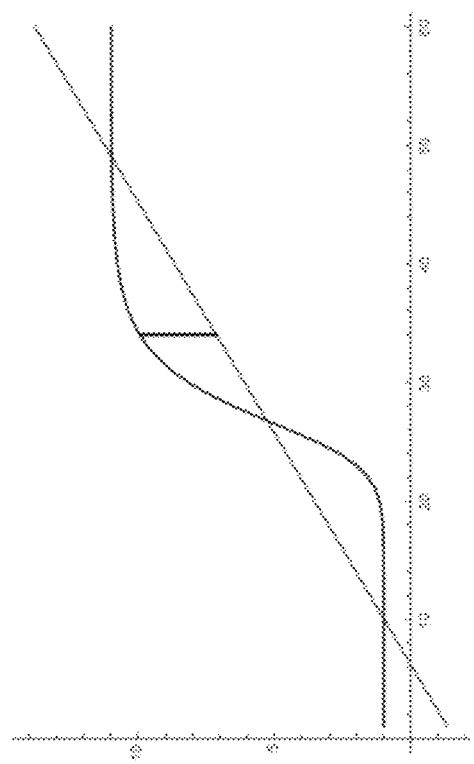
FIG. 5 is a graphical depiction of deltaB for a nucleic acid amplification growth curve.
Figure 6:
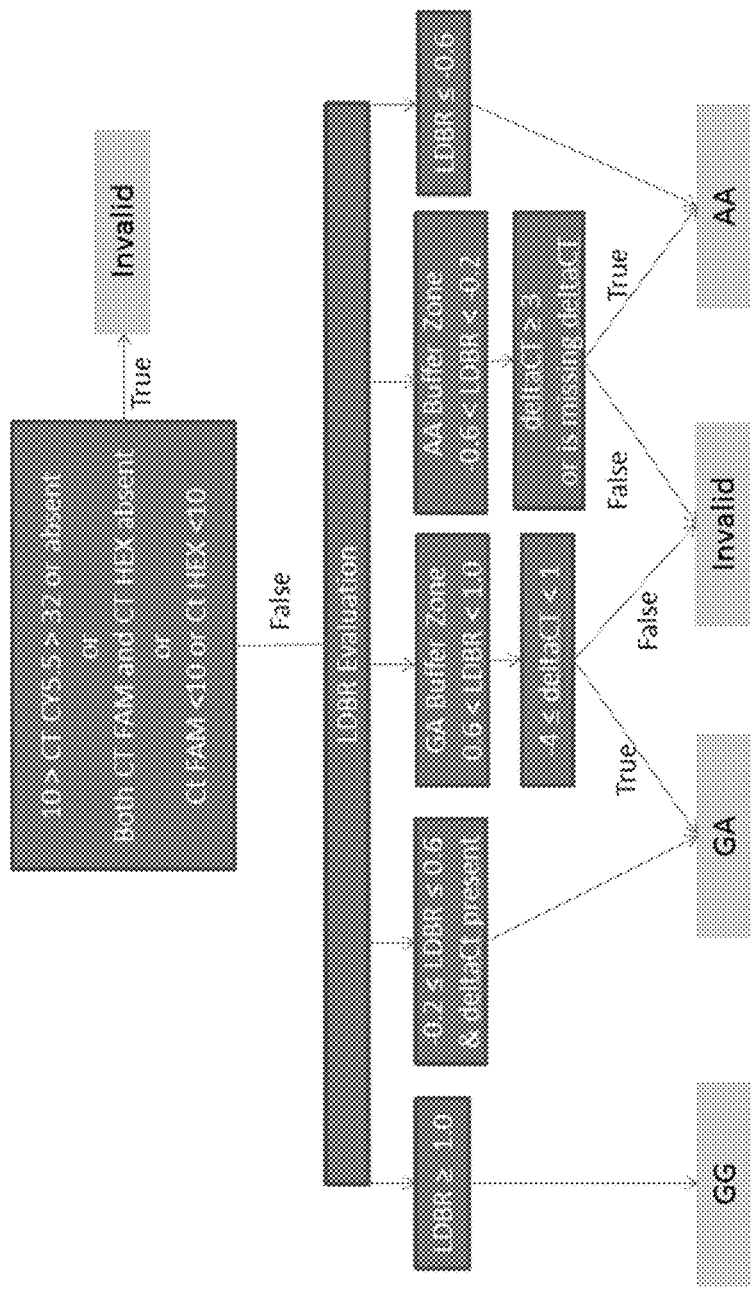
FIG. 6 illustrates the improved sequence variant method.
Figure 7:
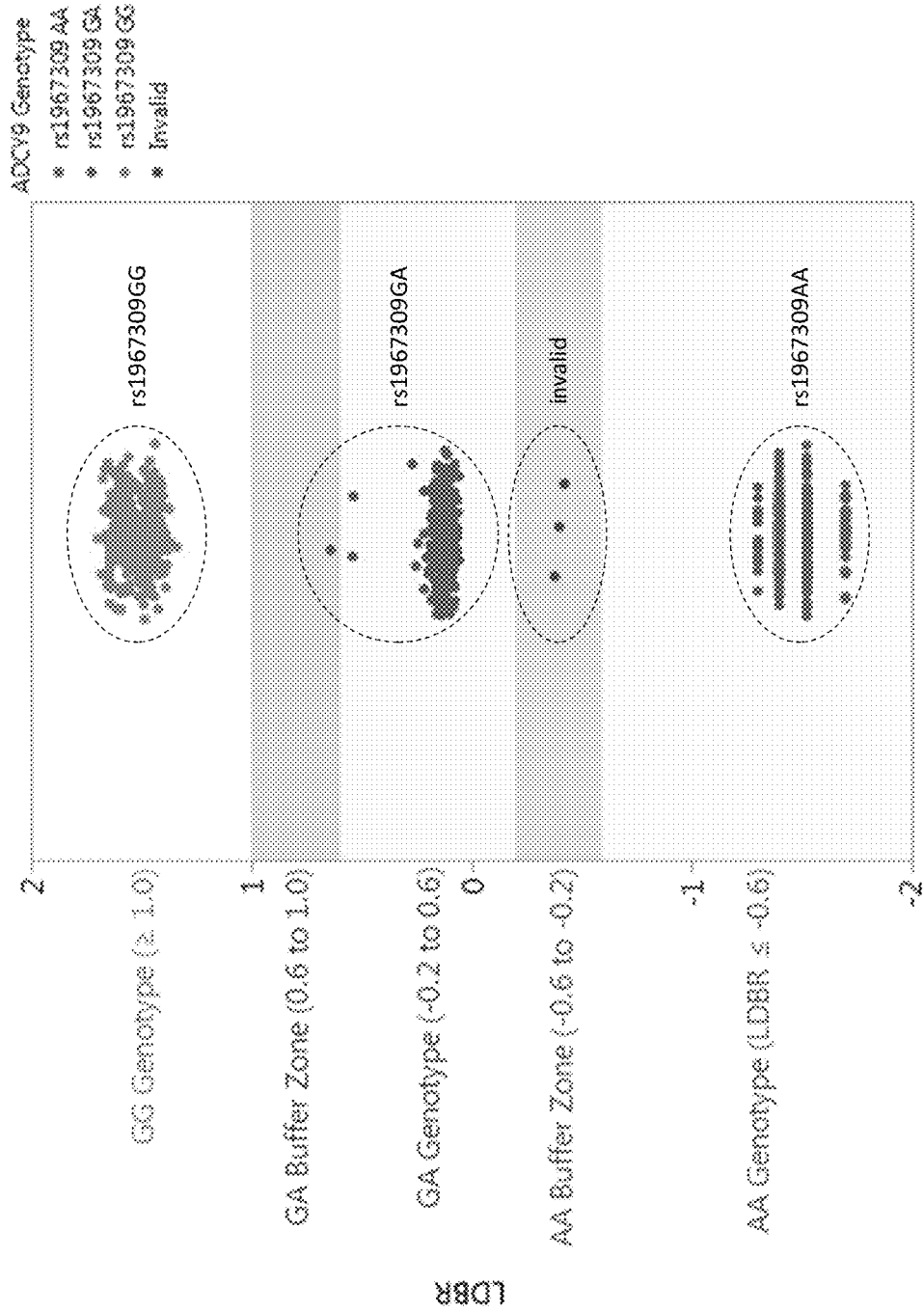
FIG. 7 shows the results obtained using the new method.

In order to develop a more robust algorithm, other algorithms were evaluated. A new algorithm was developed based on deltaB, which is defined as the relative maximum deviation from linearity of a straight line, $\hat{y}=a+bx$, from the real-time PCR data, over a range of cycle numbers, as shown in FIG. 5. The improved algorithm used Log DeltaB Ratio (LDBR) and the algorithm is schematically illustrated in FIG. 6. Results obtained using the improved algorithm are shown in FIG. 7 and as illustrated in Table 1, the new algorithm enables the RFI to be lowered relative to the conventional algorithm.

TABLE 1

RFI$_{min}$ - Old vs. New Algorithm

| Channel | Old Algorithm | New Algorithm |
| --- | --- | --- |
| CY5.5 (IC) | 6 | 5 |
| FAM (A Allele) | 2 | 0 |
| HEX (G Allele) | 2 | 0 |

CTs are set to absent for samples with RFI values below cut-offs

During sample screening using the Cobas® x480 for sample preparation, both the old and new algorithms resulted in concordant results compared to Sanger Sequencing for >99% of specimens (Table 2).

TABLE 2

Old vs. New Algorithm: Specimen Screening

| | Sanger Genotype | | |
| --- | --- | --- | --- |
| | rs1967309 AA | rs1967309 GA | rs1967309 GG |
| New Algorithm | | | |
| rs1967309 AA | 92 | 0 | 0 |
| rs1967309 GA | 0 | 129 | 1 |
| rs1967309 GG | 0 | 0 | 91 |
| Invalid | 0 | 1[b] | 0 |
| Old Algorithm | | | |
| rs1967309 AA | 92 | 0 | 0 |
| rs1967309 GA | 0 | 130 | 0 |
| rs1967309 GG | 0 | 0 | 91 |
| Invalid | 0 | 0 | 1 |

One specimen was genotyped discordant GA/invalid (new/old algorithm), compared to GG with Sanger Sequencing and one specimen was genotyped invalid/GA (new/old algorithm) compared to GA with Sanger Sequencing. Both of those specimens were inconclusive for their Sanger Genotype trace, as they exhibited only some background of the other allele and were not typically homozygous or heterozygous. Further investigation indicated that those two specimens may have been cross-contaminated during specimen collection. Using conventional methods, such inconclusive results would force the user to repeat the experiment, and if the specimens were cross-contaminated during specimen collection, the user may have to collect fresh samples to repeat the experiment.

When comparing different sample preparations with Sanger sequencing, both the old and the new algorithms showed 100% concordant results with Sanger Sequencing (Table 3). However, the old algorithm called three specimens invalid due to FAM CTR values being outside of the cut-off range for sample preparation methods with higher DNA yield.

TABLE 3

Old vs. New Genotyping Algorithm: Method Correlation

| | Sanger Genotype | | |
|---|---|---|---|
| | rs1967309 AA | rs1967309 GA | rs1967309 GG |
| New Genotype Algorithm | | | |
| rs1967309 AA | 132 | 0 | 0 |
| rs1967309 GA | 0 | 131 | 0 |
| rs1967309 GG | 0 | 0 | 131 |
| Invalid | 0 | 0 | 0 |
| Old Genotype Algorithm | | | |
| rs1967309 AA | 132 | 0 | 0 |
| rs1967309 GA | 0 | 128 | 0 |
| rs1967309 GG | 0 | 0 | 131 |
| Invalid | 0 | 3[a] | 0 |

[a]Invalidated due to FAM CTR values outside of cut-off range. New Genotype Algorithm does not use CTR.

The internal control (IC) served as a control for DNA quality and quantity. To simulate poor sample preparation, a series of challenging conditions were run, including spike-in of PCR inhibitors, sample dilution, simulation of different elution buffers, etc., and under those stress conditions, the new algorithm had 100% concordant results compared to Sanger sequencings or samples were invalidated due to poor DNA quantity or quality (Table 4). The old algorithm however, only had 97% concordant results compared to Sanger sequencing and 46 more samples (or 17%) were called invalid compared to the new algorithm (Table 4).

TABLE 4

Old vs. New Genotyping Algorithm: IC Stress Testing

| | Sanger Genotype | | |
|---|---|---|---|
| | rs1967309 AA | rs1967309 GA | rs1967309 GG |
| New Genotype Algorithm | | | |
| rs1967309 AA | 227 | 0 | 0 |
| rs1967309 GA | 0 | 269 | 0 |
| rs1967309 GG | 0 | 0 | 197 |
| Invalid | 69 | 171 | 83 |
| Old Genotype Algorithm | | | |
| rs1967309 AA | 206 | 0 | 0 |
| rs1967309 GA | 0 | 229 | 0 |
| rs1967309 GG | 0 | 19 | 189 |
| Invalid | 90 | 192 | 91 |

Figure 8:
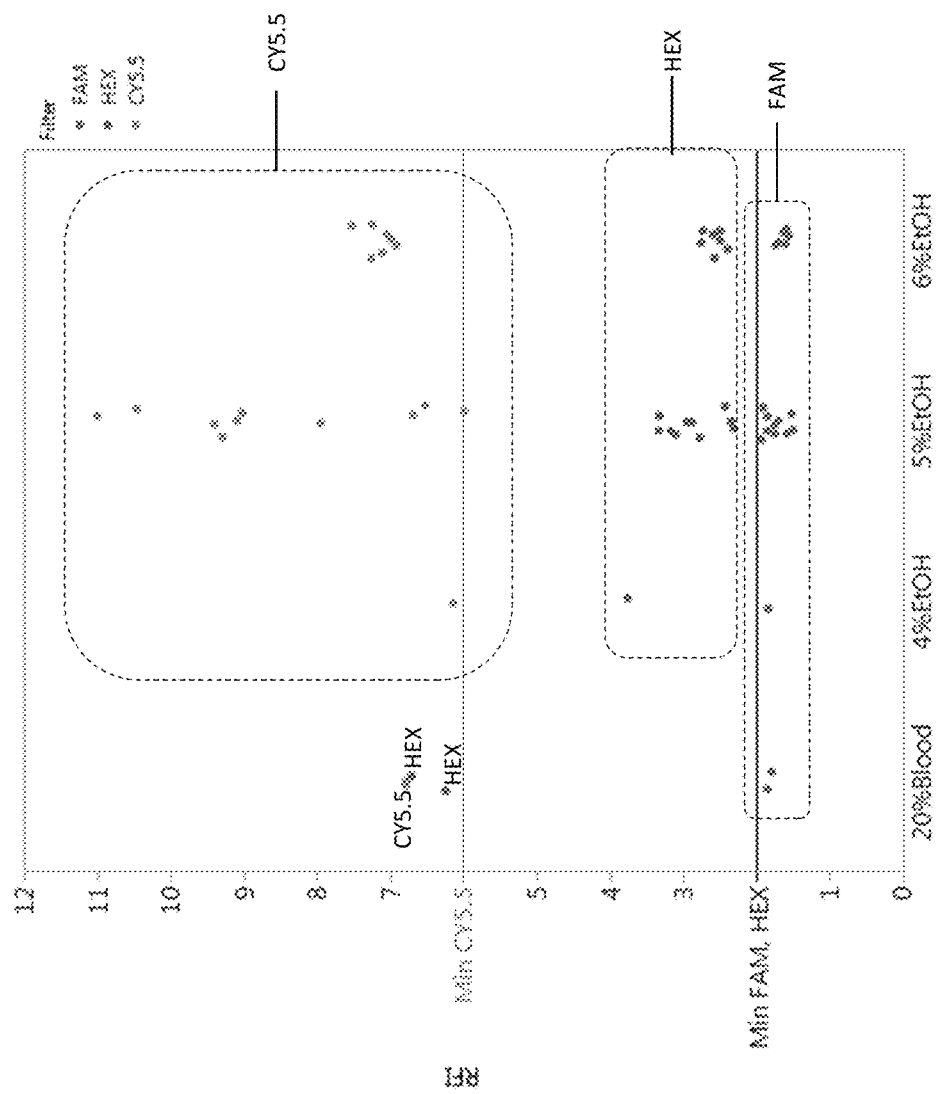
FIG. 8 shows the identification of a false GG allele using conventional sequence variant logic.

When spiking-in PCR inhibitors (blood, ethanol), 19 GA samples were incorrectly called GG with the old algorithm (Table 4). This was due to the FAM RFI values dropping below the $RFI_{min}$ cut-off and subsequently removing the CT value from the FAM channel. Thus, the samples only exhibited HEX and CY5.5 CT values and were genotyped as GG (FIG. 8). With the new algorithm, these samples are genotyped correctly.

Figure 9:
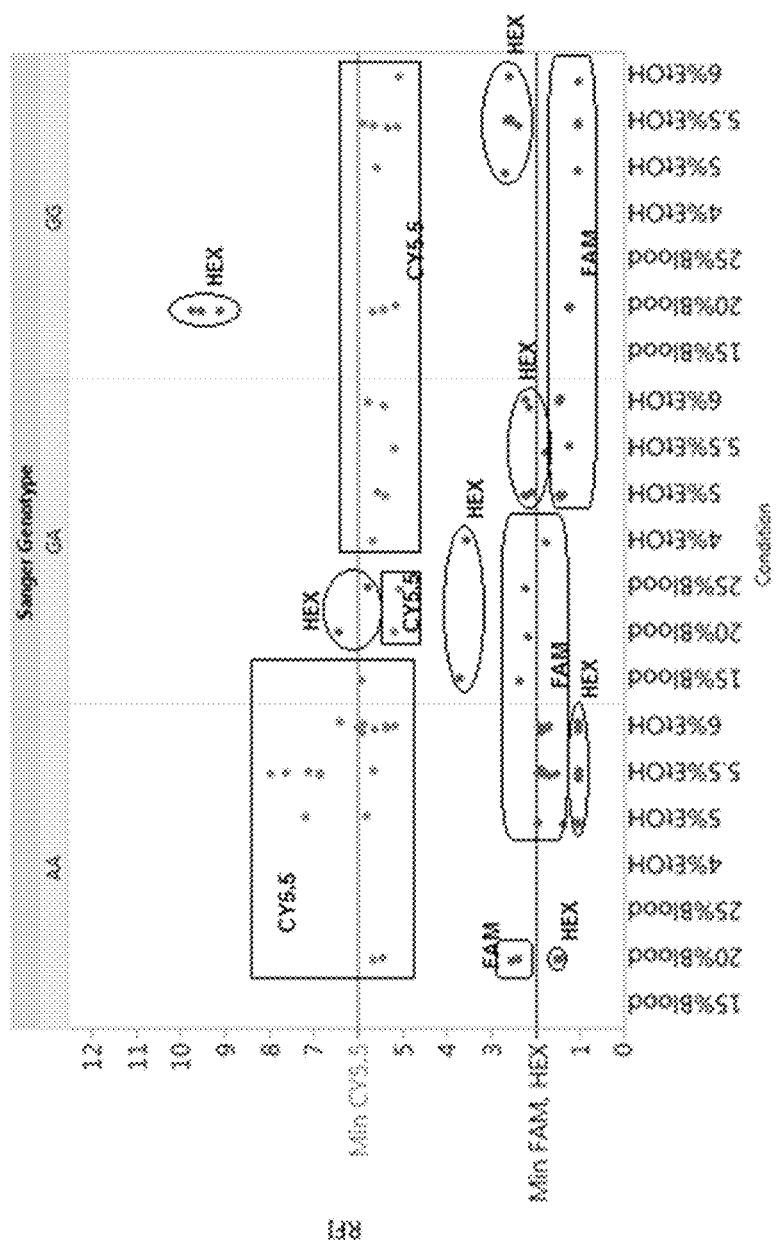
FIG. 9 shows that using conventional sequence variant logic, certain samples were invalidated due to CY5.5 or FAM RFIs (AA only) dropping below the cut-offs.
Figure 10:
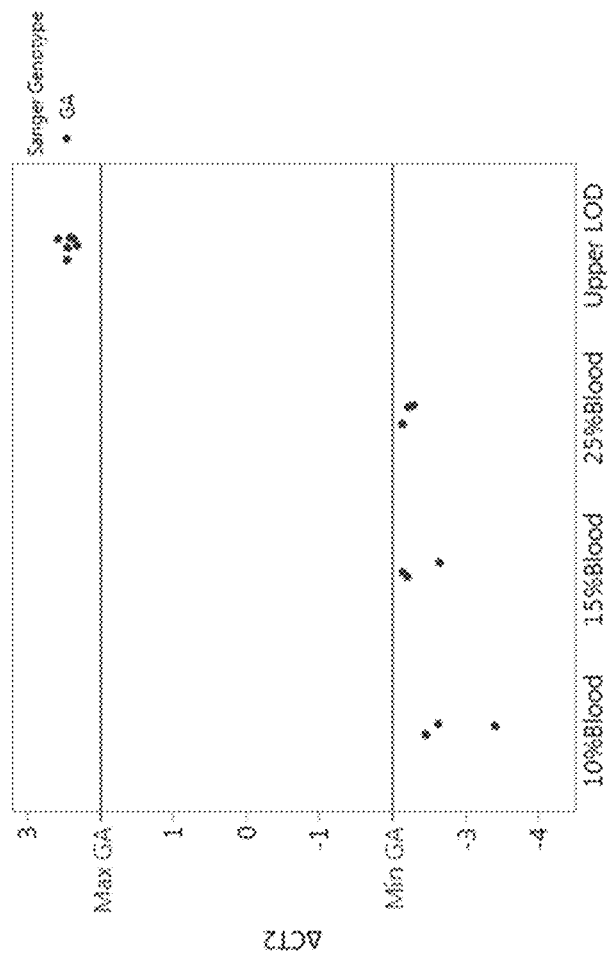
FIG. 10 shows that using conventional sequence variant logic, certain GA specimens were invalidated due to deltaCT values being outside of range.
Figure 11:
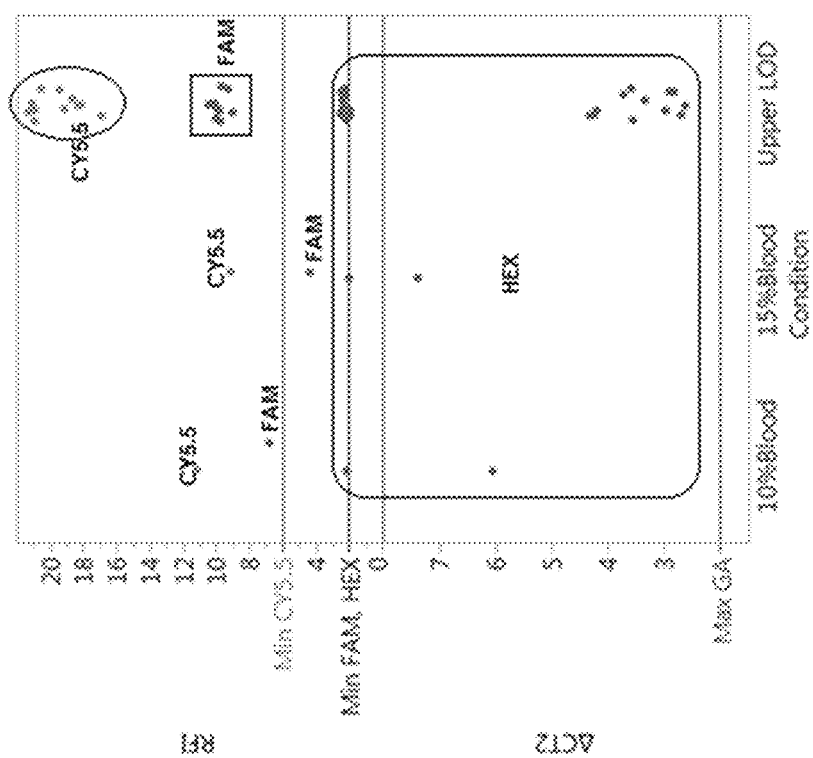
FIG. 11 shows how AA specimens were invalidated, due to HEX RFI values being above the cut-off. Samples were then treated as GA samples, because all channels (FAM, HEX and CY5.5) CTs were present, but failed the Δ CT cut-offs

More samples were invalidated with the old genotype algorithm for various reasons:

Higher $RFI_{min}$, invalidated some samples due to either CY5.5 or FAM (AA only) dropping below the cut-offs (FIG. 9), GA specimens were invalidated due to Δ CT values being outside range (FIG. 10), or AA specimens were invalidated, due to HEX RFI values being above the cut-off. Samples were then treated as GA samples, because all channels (FAM, HEX and CY5.5) CTs were present, but failed the Δ CT cut-offs (FIG. 11).

Therefore, the new genotype algorithm using LDBR was found to be more robust in identifying correct genotypes, instead of invalid or incorrect results, when challenging samples with PCR inhibitors, cross-contamination, high and low DNA concentrations, and for certain Master Mix component changes (data not shown here). The use of the old algorithm resulted in invalid results, which would have required the user to repeat experiments, which is often not possible. However, the new algorithm correctly genotyped samples that would have otherwise been found to be invalid using conventional methods.

The invention claimed is:

1. A method of detecting at least two nucleic acid sequence variants of a locus in a sample, the method comprising the steps:
   (a) amplifying, with a Polymerase Chain Reaction (PCR) system comprising a processor, the at least two sequence variants of the locus to produce at least two amplification products including a first variant amplicon and a second variant amplicon, wherein the amplifying step yields a first and second growth curve, respectively, for the first and second amplicons;
   (b) analyzing, using the processor, the first and second growth curves by calculating $deltaB_1$ for the first growth curve and calculating $deltaB_2$ for the second growth curve, wherein $deltaBn = (maximum |\hat{y}_t - y_t| / yMedian)$, and calculating a relative deviation from linearity ratio comprising $deltaB_1/deltaB_2$;
   (c) comparing, using the processor, the relative deviation from linearity ratio to a sequence-specific threshold matrix for the locus; and
   (d) identifying, using the processor, the two or more sequence variants based on said comparing step (c).

2. The method of claim 1 wherein the relative deviation from linearity ratio comprises $\log_{10}(deltaB_1/deltaB_2)$.

3. The method of claim 1 wherein the first and second growth curves are analyzed from cycle m to p, wherein 0<m<p.

4. The method of claim 3 wherein m≥2.

5. The method of claim 3 wherein 3≤m≤7.

6. The method of claim 3 wherein m=6.

7. A Polymerase Chain Reaction (PCR) system for detecting two or more nucleic acid sequence variants of a locus in a sample, the system comprising a nucleic acid amplification module operably connected to a memory, a processor, and a display, wherein the processor is configured to perform a computer-implemented method of detecting two or more sequence variants of the locus, the method comprising:
   (a) amplifying, using the nucleic acid amplification module, the at least two sequence variants of the locus to produce at least two amplification products including a first variant amplicon and a second variant amplicon,
   (b) generating, using the processor, a first and second growth curve, respectively, for the first and second amplicons;
   (c) analyzing, using the processor, the first and second growth curves by calculating deltaBi for the first growth curve and calculating deltaB2 for the second growth curve, wherein deltaBn=(maximum$|\hat{y}_i-y_i|$/yMedian), and calculating a relative deviation from linearity ratio comprising deltaB$_1$/deltaB$_2$;

(d) comparing, using the processor, the relative deviation from linearity ratio to a sequence-specific threshold matrix for the locus; and (e) identifying, using the processor, the two or more sequence variants based on said comparing step (d).

8. The system of claim 7 wherein the relative deviation from linearity ratio comprises log$_{10}$(deltaB$_1$/deltaB$_2$).

9. The method of claim 7 wherein the first and second growth curves are analyzed from cycle m to p, wherein 0<m<p.

10. The method of claim 9 wherein 3≤m≤7.

* * * * *